United States Patent [19]

Chesler

[11] 4,352,361
[45] Oct. 5, 1982

[54] DENTAL APPLIANCE CLEANING DEVICE

[76] Inventor: Richard Chesler, 531 Main St., Roosevelt Island, N.Y. 10044

[21] Appl. No.: 183,226

[22] Filed: Sep. 2, 1980

[51] Int. Cl.³ ............................................... B08B 3/02
[52] U.S. Cl. ................................... 134/58 R; 134/140; 134/148
[58] Field of Search ............... 134/58 R, 103, 108, 134/111, 140, 144, 148, 153, 176, 179, 184, 198

[56] References Cited

U.S. PATENT DOCUMENTS

| | | | |
|---|---|---|---|
| 2,764,171 | 9/1956 | Nolte | 134/153 X |
| 2,994,330 | 8/1961 | Catlin et al. | 134/58 R |
| 3,236,249 | 2/1966 | Everroad | 134/179 X |
| 3,630,804 | 12/1971 | Coffman et al. | 134/153 X |

FOREIGN PATENT DOCUMENTS 2033735  5/1980  United Kingdom ................ 134/179

*Primary Examiner*—Robert L. Bleutge

[57] ABSTRACT

A dental appliance cleaning device which includes a housing having at least one chamber therein, wherein a receptacle can be removably inserted into the chamber of the housing such that at least one dental appliance is receivable into the receptacle, wherein a mechanism for rotating the receptacle within the housing can be provided. A mechanism for cleaning the dental appliance within the receptacle is provided, wherein the cleaning mechanism is a mechanism for spraying a cleaning liquid on the dental appliances disposed within the receptacle.

14 Claims, 10 Drawing Figures

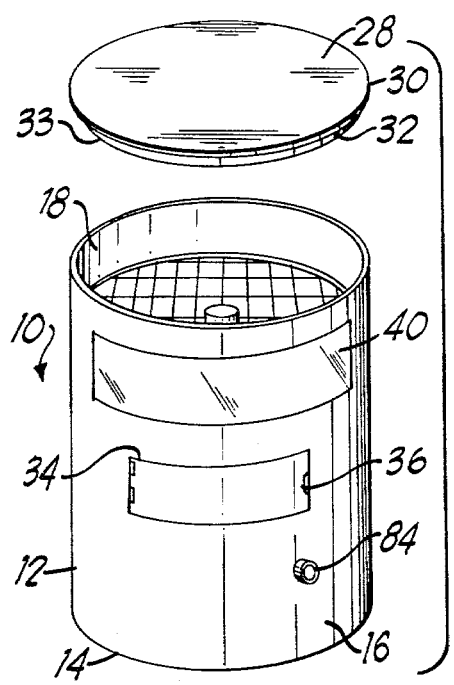
FIG.1
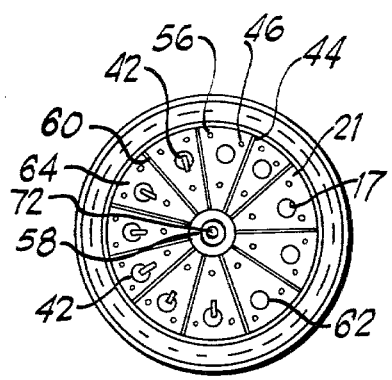
FIG.2A
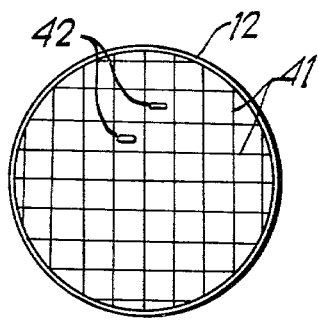
FIG.2B
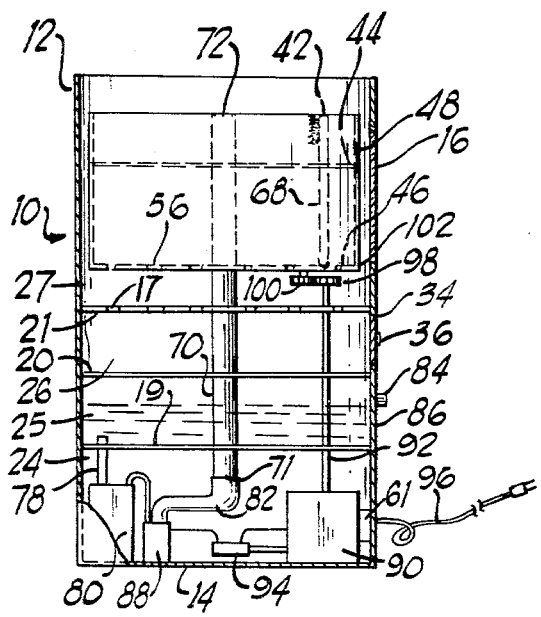
FIG.3
FIG.4

4,352,361

DENTAL APPLIANCE CLEANING DEVICE

FIELD OF THE INVENTION

A dental appliance cleaning device which includes a housing having at least one chamber therein, wherein a receptacle can be removably inserted into the chamber of the housing such that at least one dental appliance is receivable into the receptacle, wherein a mechanism for rotating the receptacle within the housing can be provided. A mechanism for cleaning the dental appliance within the receptacle is provided, wherein the cleaning mechanism is a means for spraying a cleaning liquid on the dental appliance disposed within the receptacle.

BACKGROUND OF THE INVENTION

A number of U.S. patents relate to general field of cleaning dental appliances such as toothbrushes, but these U.S. patents are distinguishable from the instant invention. These U.S. Pat. Nos. are: 1,224,696; 1,507,466; 1,566,860; 2,280,431; 3,867,096; 3,881,888; and 4,050,894.

SUMMARY OF THE INVENTION

A dental appliance cleaning device which includes a housing having at least one chamber therein, wherein a receptacle can be removably inserted into the chamber of the housing such that at least one dental appliance is received into the receptacle, wherein a mechanism for rotating the receptacle within the housing can be provided. A mechanism for cleaning the dental appliance within the receptacle is provided, wherein the cleaning mechanism is a means for spraying a cleaning liquid on the dental appliance within the receptacle.

BRIEF DESCRIPTION OF THE DRAWINGS

The objects and features of the invention may be understood with reference to the following detailed description of an illustrative embodiment of the invention, taken together with the accompanying drawings in which:

FIG. 1 illustrates a perspective view of the invention;

FIG. 2A illustrates a top view of the invention with the top cover removed, wherein the dental appliances are stationary;

FIG. 2B illustrates a top view of the invention with the top cover removed, wherein the dental appliances can be rotated;

FIG. 3 illustrates a side partially cut away view of the invention;

FIG. 4 illustrates a partially cut away view of the drum shaped member of the invention;

DESCRIPTION OF THE PREFERRED EMBODIMENT

Figure 5:
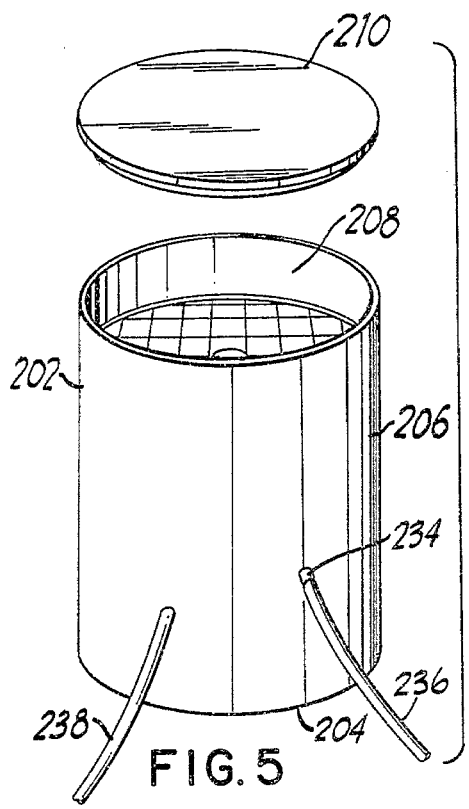
FIG. 5 illustrates a perspective view of a third embodiment of the invention.

Turning now descriptively to the drawings, in which similar reference characters denote similar elements throughout the several views, FIGS. 1–4 show a dental appliance cleaning device 10 generally including a housing 12 having a base 14, at least one upwardly extending wall 16, an open top 18, three internally, horizontally disposed platforms 19, 20, 21 thereby forming a lower 24, a lower center 25, an upper center 26, and an upper 27 compartments therein, wherein the uppermost platform 21 has a plurality of holes 17 therethrough. A removable top cover 28 generally includes a disc shaped element 30 having a cylindrically shaped wall 32 extending downwardly therefrom, wherein the external surface 33 of the downwardly extending wall 32 is externally threaded. The top cover 28 is removably received into the open top 18 of housing 12, wherein the externally threaded surface 33 of downwardly extending wall 32 threadably engages a threaded upper interior surface of upwardly extending wall 16 of housing 12. The upwardly extending wall 16 contains an opening 34 therein, wherein opening 34 is in communication with the upper center compartment 26. A panel member 36 is removably received into opening 34, wherein panel member 36 can be hingably secured to upwardly extending wall 16 of housing 12 or alternatively is secured by snap means to the upwardly extending wall 16 of housing 12 or even alternatively to the aforementioned, panel member 36 forms the front portion of a drawer member which is slidably received into the upper center compartment 24 such that the used cleaning fluid 86 can be collected in the upper center compartment 26 or drawer member.

In place of the panel 36 or drawer member, a drainage value member can be disposed in the upwardly extending wall 16 of the housing, wherein the drainage value member is in direct serial fluid communication with the upper center compartment 26 or in serial fluid communication with upper center compartment 26 by means of a tube extending through one or more of the other compartments 24, 25, 26. Optionally, a transparent window member 40 can be disposed in the upwardly extending wall 16, wherein window member 40 is aligned with the upper compartment 27. Disposed within the upper compartment 27 is a means for holding a plurality of dental appliances 42 such as toothbrushes in a vertical alignment with the upper compartment 27. In one embodiment as depicted in FIG. 2B, a plurality of elongated members 41 are horizontally disposed in the upper compartment 27 in a crisscross configuration, wherein the ends of the elongated members 41 are affixed to an upper interior surface of the upwardly extending wall 16 of the housing 12 thereby permitting the toothbrushes 42 to be inserted in a vertical alignment between the elongated members 41. A further modification of the means for holding the dental appliances 42 comprises a means for rotating the dental appliances 42 while maintaining the dental appliances 42 in the vertical alignment with the upper compartment 27. This rotating means generally includes a drum member 44 disposed within the upper compartment 27 and a means for rotating the drum member 44. The drum member 44 generally includes a base 46 having a plurality of apertures 56 therethrough, an upwardly extending cylindrically shaped wall 48, an open top 50 and a chamber 52 therein. As seen in FIG. 2A, a hub 58 having a plurality of radially extending spokes 60 is horizontally disposed in an upper portion of chamber 52 of drum member 44, wherein the outer ends of spokes 60 are affixed to upwardly extending wall 48 of drum member 44 thereby forming a plurality of openings 64 between the spokes 60. A plurality of annularly shaped members 62 are affixed onto an upper surface of base 46 of drum member 44, wherein the annularly shaped members are aligned under the openings 64. The toothbrushes 42 are removably disposed in a vertical alignment within openings 64, wherein the handle end 66 of stem 68 of the toothbrushes 42 are removably received into the annularly shaped members 62. An elongated tubular element 70 having a continuous bore therethrough is disposed within housing 12 in a vertical alignment, wherein the lower end 71 of tubular element 70 extends downwardly through the lower most platform 19 into the lower most compartment 24 and the tubular element 70 extends upwardly through the center platform 20, the uppermost platform 21 and through the base 46 of drum member 44 and the hub 58, wherein base 46 and hub 58 are journalled for rotation on tubular element 70. The upper end 72 of tubular element 70 is closed and the sidewall 74 of tubular element 70 between hub 58 and base 46 of drum member 44 has a plurality of holes 76 therethrough. A plurality of spray head means 79 can be disposed in holes 76. One end of a first elongated tube member 78 is disposed within the lower center compartment 25 and extends downwardly through the lower most platform 19 into the lower compartment 24, wherein the other end of the elongated tube member 78 is joined in a serial fluid connected to a pump means 80. One end of a second elongated tube member 82 disposed in lower compartment 27 is joined in serial fluid communication to a pump means 80, wherein the other end of the second elongated tube member 82 is joined in a serial fluid communication to the lower end 71 of the tubular element 70. Obviously, the second elongated tubular member 82 could extend upwardly through the lower center compartment 25, upper center compartment 26 and into the upper compartment 27, wherein the other end of the second elongated tube member 82 could be joined at any given selected point to tubular element 70 or even tubular element 70 could be shortened to extend only into the upper center compartment 26 in the case wherein drawer member 38 is employed. Referring back to the pump means 80, it can be of a purely mechanical design with a crankshaft (not shown) and handle extending outwardly through the upwardly extending wall 16 of the housing 12 or alternatively and preferably the pump means 80 is an electrically operated pump as shown, wherein the electrically powered pump 80 is powered by battery means or by an external electrical power source. An inlet port or inlet value means 84 is disposed in the upwardly extending wall 16 of housing 12, wherein inlet value means 84 is in serial fluid communication with the lower center compartment 25 which has the cleaning fluid 86 disposed therein, wherein the value means 84 permits the further injection of cleaning fluid 86 into the lower compartment 25. The cleaning fluid 86 is pumped by pump means 80 from the lower center compartment 25 upwardly through the tubular element 70 and sprayed outwardly through the holes 76 or spray head means 79 thereby impigning a continuous spray onto the dental appliances 42 disposed in the upper compartment 27 or in the drum member 44 disposed in the upper compartment 27 so as to clean the dental appliances 42. The cleaning fluid 86 draining off of the cleaned dental appliance drains through the apertures 56 in base 46 of drum member 44 and subsequently through holes 17 in the upper most platform 21 into the upper center compartment 26 or drawer member for subsequent disposal. Optionally, a heating element 88 can be disposed in serial fluid communication within either the first 70 or second 82 elongated tube member thereby allowing the cleaning fluid 86 to be heated prior to being sprayed, wherein the heating element 88 is disposed in the lower compartment 24. For illustrative purposes, the cleaning fluid 86 can be water or a solution of water or even alcohol with an antiseptic. The means for rotating drum member 44 generally includes, in the case of the pump means being operated by the crank handle means, a gear train assembly communicating between the crank handle means and the drum member. The means for rotating the drum member 44 can include an electric motor 90 having an upwardly extending vertically disposed drive shaft 92, wherein the electric motor 90 is disposed within the lower compartment 24. The upwardly extending drive shaft 92 extends upwardly through the lower platform 19, center platform 20 and upper platform 21 into the upper most compartment 27 below the base 46 of drum member 44 or to the side of drum member 44. To the upper end of the vertical drive shaft 92 within the upper most compartment 27 is affixed a first gear member 98. A second gear member 100 is affixed onto a shaft 102 which is affixed onto base 46 of drum member 44 and extends vertically and downwardly therefrom, wherein gear members 98, 100 mesh together thereby permitting continuous or intermediate rotation of the drum member 44 to occur.

Obviously, the electrical motor 90 can be disposed in the upper compartment as well as the pump means 80 thereby consolidating the upper 27 and lower 24 compartments together. A further obvious modification is the consolidation of the center two compartments 25, 26 in one chamber subdivided by vertical panel into two subchambers. When the electric motor 90 is disposed in the upper most compartment 27 the drive shaft 92 can be vertically aligned with the same arrangement of gear members 98, 100 or alternatively the drive shaft 92 can be horizontally disposed (not shown) and in communication with a beveled gear train assembly (not shown) which in turn is in communication with the drum member 44. An alternative embodiment is an annular gear member (not shown) affixed onto an outer surface of upwardly extending sidewall 48 of drum member 44, wherein gear member 98 meshes with the annular gear member. Means is provided for forming liquid tight junctures between the platforms 19, 20, 21 and drive shaft 92 as well as the tubular element 70 and the first 78 and second 82 elongated tube members.

The electrical motor 92, the heating element 88 and the pump means 80 are wired in a parallel circuit to a common electrical juncture box 94, wherein an electrical power cord 96 is wired to box 94 and extends outwardly through the upwardly extending sidewall 16 of the housing 12.

An electrical time device 61 can be disposed in the electric power cord 96 thereby providing a means for interrupting the current to the pump means 80, heating element 88 and electric motor 92 after a predetermined time so as to enable the user to select a predetermined length of time for the dental appliance cleaning device 10 to operate.

It is contemplated within the instant invention that a means (not shown) could be provided wherein the drum member 44 is alternately moved upwardly and downwardly within the upper compartment 27 while the drum member 44 is rotating within the upper compartment thereby ensuring a more uniform application of cleaning fluid spray on the dental appliances 42 disposed within the drum member 44. Obviously, a means (not shown) can be also provided whereby the tubular element 70 is continuously rotated while the drum member 44 is maintained in a stationary position within upper compartment 27.

Alternatively, but less preferably to the use of the pump means 80, the cleaning fluid could be stored in the upper compartment 27 and feed by gravity to the drum member 44 which would be disposed in this case in the lower compartment 27, wherein the cleaning fluid 86 would impign on the toothbrushes 42.

An alternate means for delivering the spray of cleaning fluid 86 within drum member 44 comprises a rotary spray means (not shown) disposed within the chamber of drum member 44 and secured onto the base 46 of drum member 44. The holes 76 within tubular element 70 as well as the spray head means 79 are not provided. The rotary spray means is joined in serial fluid communication to tubular element 70 by a connecting tube (not shown). The rotary spray means can be generally described as a miniaturized rotary lawn sprinkler device having at least one nozzle unit which is caused to rotate by water pressure and to emit a continuous spray of liquid. This rotary spray means is depicted, for example, in U.S. Pat. Nos. D238,670, D244,936, D200,950 which are incorporated herein by reference. Obviously other rotary spray means of various designs can be used and are envisioned within the spirit and scope of the instant invention.

Figure 6:
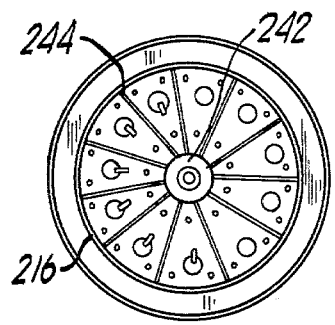
FIG. 6 illustrates a top view of FIG. 5.
Figure 7:
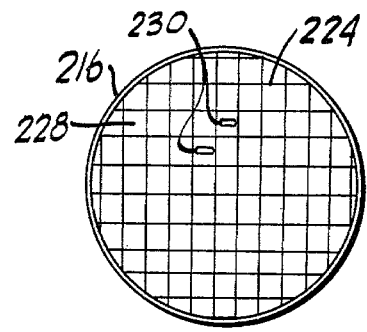
FIG. 7 illustrates a top view of FIG. 5.
Figure 8:
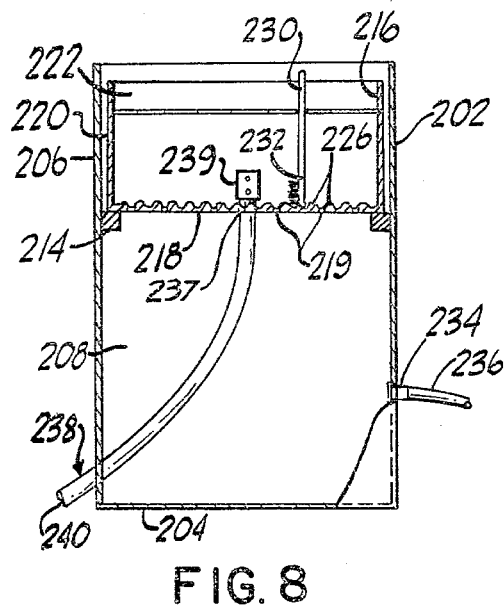
FIG. 8 illustrates a partially cut away view of FIG. 5.
Figure 9:
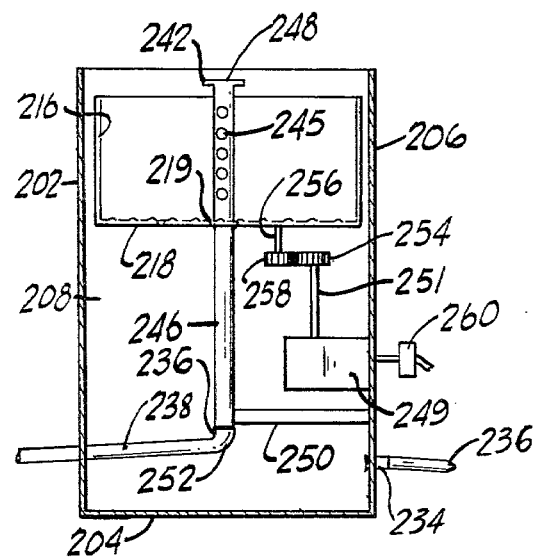
FIG. 9 illustrates a partially cut away view of FIG. 5.

In a second simplified embodiment of the invention, the dental cleaning device 201 as shown in FIGS. 5-9 generally includes a housing 202 having a base 204, at least one upwardly extending wall 206, and a chamber 208 therein, wherein the upper interior surface of the upwardly extending wall 206 of the housing 202 is internally threaded, wherein a threaded cap member 210 threadably engages the threaded interior surface of the upwardly extending wall 206 of the housing 202. An annular shaped flange member 214 is affixed to the interior surface of the upwardly extending wall 206 of housing 202. A drum shaped member 216 having a base 218 with a plurality of holes 219 therethrough, an upwardly extending wall 220, a chamber therein 222, and an open top is removably received into the chamber 208 of housing 202, wherein the base 218 of the drum shaped member 216 rest on the annular shaped flange member 214. A plurality of elongated members 224 are horizontally disposed in the upper portion of the chamber 22 of the drum shaped member 216, wherein the elongated members 224 are arranged in a crisscross arrangement, wherein the ends of the elongated member 224 are affixed to the upper extending wall 220 of the drum shaped member 216. The upper surface of base 218 of the drum shaped member 216 has a plurality of indentations 226 therein, wherein the indentations 226 are aligned under the spaces 228 formed between the elongated members 224. The dental appliance 230 such as toothbrushes are removably received in a vertical alignment with the chamber 222 of the drum shaped member 216, wherein the handle end of the stems 232 of the toothbrushes 230 extend upwardly through the spaces 228 and the head end of the stem 232 of the toothbrushes 230 rest in the indentations 226 thereby providing a means for maintaining the dental appliance 230 in the vertical alignment within the chamber 222 of the drum shaped member 216. A drainage value 234 is disposed in the lower end of upwardly extending wall 206, wherein a drainage hose 236 is detachably secured to drainage value 234. One end 237 of an elongated tubular member 238 extends through upwardly extending wall 206 and extends into chamber 222 of the drum shaped member 216, wherein a spray nozzle means 239 is affixed onto end 237 of the elongated tubular member 238. The other end 240 of the elongated tubular member 238 is in serial fluid communication with a continuous water supply means (not shown) such as a faucet. Alternatively, (not shown) end 237 of elongated tubular member 238 can extend through threaded cap member 210 such that end 237 of the elongated tubular member 238 extends into the chamber 222 of the drum shaped member 216.

Additionally (not shown) a means can be provided for continuously metering a cleaning fluid into elongated tubular member 238 such as a liquid injection means (not shown). Alternatively, a means for rotating the drum shaped member 216 within the chamber 208 of the housing 202 is provided. In this embodiment the elongated members 224 are replaced by a hub 242 having a plurality of radially outwardly extending and horizontally aligned spoked 244, wherein the ends of the spoked 244 are affixed to the upwardly extending wall 220 of the drum shaped member 216 and the hub 242 has a hole 245 therethrough. The base 218 of drum shaped member 216 has a center hole 219 therethrough. An elongated tubular element 246 is vertically disposed in chamber 208, wherein the upper closed end 248 of element 246 extends upwardly through hole 219 and hub 242 such that drum member 216 is rotatably disposed on tubular element 246. A bracket member 250 is disposed in chamber 208 of housing 202 and is affixed onto the lower open end 252 of tubular element 246. The tubular element 246 has a plurality of holes 245 between the point at which the tubular element 246 extends through base 218 of drum shaped member 216 and hub 242. End 236 of the elongated tubular member 238 is joined in serial fluid communication with the lower end 252 of tubular element 246. A waterproof electrical motor 249 having a vertically disposed shaft 251 is disposed within chamber 208 below the drum shaped member 216, wherein a first gear member 254 is affixed onto the vertically aligned drive shaft 251. A shaft member 256 is affixed to base 218 of the drum shaped member 216 and extends downwardly therefrom into chamber 208 below the drum shaped member 216. A second gear member 258 is disposed on shaft member 256, wherein gear members 254, 258 mesh together. The electrical motor 249 can be optionally wired in series to electric timed turn off delay device 260 which will automatically interrupt the current to the electric motor 249 after a determined time. In use the water supply means is activated thereby causing a continuous spray of water or cleaning solution to be continuously sprayed onto the dental appliances 230 which drains off the dental appliances 230 through the holes 219 of base 218 of the drum shaped member 216 into chamber 208 of housing 202 and eventually outwardly through drainage value 234. Additionally, a means can be provided for pulsating the water flow within the elongated tubular member 238 thereby causing the spray impigning upon the dental appliances 230 to be in a repetitive pulsing manner. As in the first embodiment of the invention, a means can be provided for rotating the tubular element 246 while maintaining drum shaped member 216 in a stationary position. Additionally, as in the first embodiment of the invention a means can be provided for moving the drum shaped member 216 upwardly and downwardly in a vertical direction within the chamber 208 of the housing 202.

Obviously, also a heating means (not shown) can be provided in tubular member 236 for heating the water.

Since obvious changes may be made in the specific embodiment of the invention described, such modification being within the spirit and scope of the invention claimed, it is indicated that all matter contained herein is intended as illustrative and not as limiting in scope.

What is claimed is:

1. A dental appliance cleaning device which consists of:
   (a) a housing having an open top and at least one chamber therein;
   (b) a receptacle insertable into said chamber of said housing, said receptacle capable of receiving at least one dental appliance therein;
   (c) spray means for cleaning said dental appliance within said receptacle with a cleaning fluid, said cleaning fluid being in liquid contact with said dental appliance; and
   (d) means for rotating said receptacle within said housing.

2. A dental appliance cleaning device according to claim 1, wherein said rotating means consists of:
   (a) an electrical motor having a drive shaft, said electrical motor being disposed in said chamber of said housing;
   (b) a first gear member affixed onto said drive shaft of said electrical motor;
   (c) a second gear member in communication with said receptacle, said second gear member meshing together with said first gear member; and
   (d) an elongated cylindrically shaped member affixed to a base of said housing and extending upwardly from said base within said chamber of said housing; said receptacle being rotatably disposed on said elongated cylindrically shaped member.

3. A dental appliance cleaning device according to claim 1, further including a means for controlling the length of time of the spraying of said dental appliances.

4. A dental appliance cleaning device according to claim 1, wherein said spraying means consists of:
   (a) an elongated tubular member having a continuous bore therethrough, one end of said elongated tubular member being open, another end of said elongated tubular member being closed, a sidewall of said elongated tubular member having a plurality of holes therein, said closed end of said elongated tubular member extending into a chamber of said receptacle;
   (b) a pump means disposed within said chamber of said housing, said pump means being in serial fluid communication with said open end of said elongated tubular member; and
   (c) means for storing said cleaning fluid within said housing, said storage means being in serial fluid communication with said pump means.

5. A dental appliance cleaning device according to claim 4, further including a means for controlling the length of time of the spraying of said dental appliances.

6. A dental appliance cleaning device according to claim 1, wherein said spary means comprises:
   (a) an elongated tubular member having a continuous bore therethrough, one end of said elongated tubular member extending into a chamber of said receptacle;
   (b) a rotary spray means disposed within said receptacle, said rotary spray means being in serial fluid communication with said elongated tubular member;
   (c) a pump means disposed within said chamber of said housing, said pump means being in serial fluid communication with said elongated tubular member; and
   (d) means for storing said cleaning fluid within said housing, said storage means being in serial fluid communication with said pump means.

7. A dental appliance cleaning device according to claim 6, further including a plurality of spray head means, one of said spray head means being disposed in each of said holes of said elongated tubular member.

8. A dental appliance cleaning device according to claim 7, further including a means for heating said cleaning fluid prior to said spraying.

9. A dental appliance cleaning device according to claim 8 further including a means for collecting said cleaning fluid subsequent to cleaning of said dental appliances.

10. A dental appliance cleaning device according to claim 1 wherein said rotating means further consists of:
    (a) an electric motor having a drive shaft, said electrical motor being disposed in said chamber of said housing;
    (b) a first gear member affixed onto said drive shaft of said electrical motor; and
    (c) a second gear member in communication with said receptacle, said second gear member meshing together with said first gear member, said receptacle being rotatably disposed on said elongated tubular member within said chamber of said housing.

11. A dental appliance cleaning device according to claim 1, wherein said spraying means consists of:
    (a) an elongated tubular member having a continuous bore therethrough;
    (b) an elongated hose member in serial fluid communication with said elongated tubular member, said hose member extending outwardly through said housing, said elongated hose member being adaptably received on a faucet; and
    (c) a spray means being in serial fluid communication with said elongated tubular member within said receptacle.

12. A dental appliance cleaning device according to claim 11, wherein said rotating means further consists of:
    (a) an electric motor having a drive shaft, said electrical motor being disposed in said chamber of said housing;
    (b) a first gear member affixed onto said drive shaft of said electrical motor; and
    (c) a second gear member in communication with said receptacle, said second gear member meshing together with said first gear member, said receptacle being rotatably disposed on said elongated tubular member within said chamber of said housing.

13. A dental appliance cleaning device according to claim 12, further including a means for removing said cleaning fluid from said dental appliance cleaning device subsequent to said cleaning fluid being sprayed on said dental appliances.

14. A dental appliance cleaning device according to claim 13, further including a means for controlling the length of time of the spraying of said dental appliances.

* * * * *